United States Patent [19]

Vacek

[11] 4,362,876

[45] Dec. 7, 1982

[54] PREPARATION OF DIHYDROXYQUINOLINE AND CERTAIN DERIVATIVES

[75] Inventor: Lubomir Vacek, Toledo, Ohio

[73] Assignee: The Sherwin-Williams Company, Cleveland, Ohio

[21] Appl. No.: 932,912

[22] Filed: Aug. 11, 1978

[51] Int. Cl.³ ............... C07D 215/54; C07D 215/22
[52] U.S. Cl. .................................................. 546/155
[58] Field of Search ........ 260/287 H, 289 R, 283 CN, 260/283 SY; 546/155

[56] References Cited

U.S. PATENT DOCUMENTS

| 3,485,845 | 12/1969 | Davis | 546/156 |
| 4,119,720 | 10/1978 | Hardtmann | 546/155 |
| 4,124,587 | 11/1978 | Hardtmann | 546/155 X |
| 4,127,574 | 11/1978 | Hardtmann et al. | 546/155 X |
| 4,175,193 | 11/1979 | Kadin | 546/153 |
| 4,221,797 | 9/1980 | Hardtmann et al. | 546/153 X |

FOREIGN PATENT DOCUMENTS 47-45750  2/1970  Japan .

OTHER PUBLICATIONS

Staiger, et al., J. Org. Chem. 24, pp. 1214–1219 (1959).
Kadin, et al., Synthesis, 1977, (7), pp. 500–501, 7/77.
Coppala, et al., J. Org. Chem., vol. 41, No. 5, pp. 825–831 (1976).
Morrison et al., Organic Chemistry, (1966) pp. 660–669.

Elderfield, "Heterocyclic Compounds", (1957), p. 58.

Primary Examiner—Donald G. Daus
Assistant Examiner—Diana G. Rivers
Attorney, Agent, or Firm—John C. Purdue; Robert E. McDonald

[57] ABSTRACT

There is disclosed a process for the preparation of dihydroxyquinoline and certain derivatives thereof. The compounds have the structure:

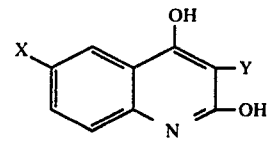

where
X = Cl, Br, I, $NO_2$, H
Y = —CN, —H —COOH

The process comprises the reaction of isatoic anhydride or its derivatives with alkyl esters of cyanoacetic acid to form an intermediate compound such as 2-(2'-aminobenzoyl)cyanoacetate which subsequently undergoes cyclization to form 3-cyano-2,4-diydroxyquinoline (when X is hydrogen) or its derivatives (where X is Cl, Br, I or $NO_2$). The cyano group may be cleaved under alkaline conditions to convert Y from —CN to —H or under acid conditions to convert Y from —CN to —COOH.

3 Claims, No Drawings

PREPARATION OF DIHYDROXYQUINOLINE AND CERTAIN DERIVATIVES

BACKGROUND OF THE INVENTION

There are many prior art processes for preparing dihydroxyquinoline and derivatives thereof.

The oldest method uses Doebuer-Miller's reaction, and is based on melting N-acetylanthranilic acid with a mixture of NaOH, KOH, NaNH$_2$ at 150° to 190° C. The following reaction equation is illustrative.

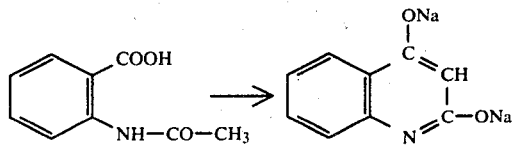

This is a high yield method but requires NaNH$_2$, a chemical which is highly hazardous because of (1) Spontaneous explosion of NaNH$_2$ itself or (2) Occurrences of explosions in case of a trace of water present in the reaction mixture. This process is disclosed in German Pat. No. 117,167.

Another preparative method is based on the cyclization of ethyl N-acetylanthranilate by means of metallic sodium. The yield is relatively low, about 30 to 40 percent of the theory. The method is illustrated by the following equation.

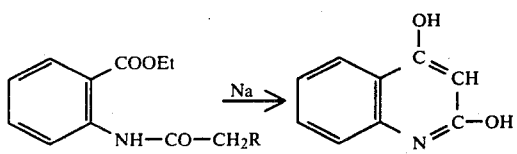

A further preparative method is based on the cyclization of the condensation product of 1 mole of ethyl anthranilate with 1 mole of diethylmalonate by means of sodium methoxide, followed by saponification and decarboxylation. This method produces higher yields of dihydroxyquinoline, but of lower purity as a consequence of unclean condensation of malonate with ethyl anthranilate. The following reactions illustrate the process.

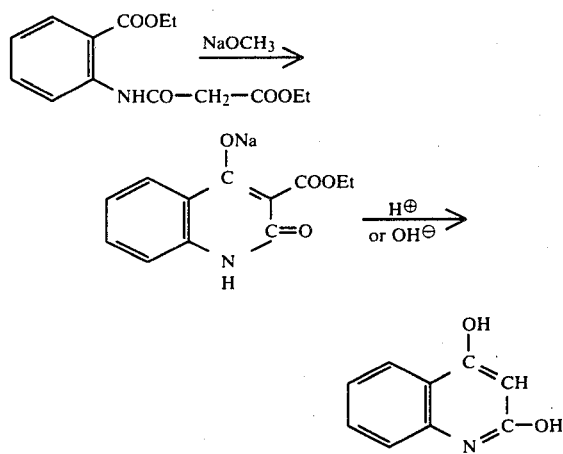

In recently issued U.S. Pat. No. 3,642,571, assigned to BASF, there is disclosed the preparation of 2,4-dihydroxyquinolines based on treatment of 2-substituted benzoxazinones-4 with alkali metal alkoxides or sodium piperidine at temperatures from room to about 200° C.

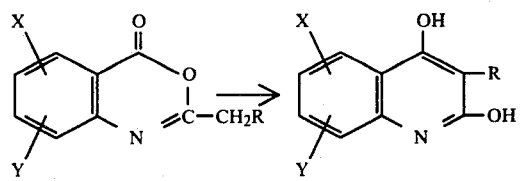

R=H, or an electron attracting group (CH$_3$—CO—)

The starting benzoxazinone-4 is prepared from anthranilic acid through reaction with acetic anhydride or diketene.

Other recent patents, also assigned to BASF, U.S. Pat. Nos. 3,682,928 and 3,753,991, disclose a process for the production of 2,4-dihydroxyquinoline based on the cyclization of N-acetoacetylanthranilic acid ester with an aqueous solution of 1-10 equivalents of alkali-or alkaline earth hydroxides, followed by deacetylation of the formed 3-acetyl-2,4-dihydroxyquinoline by means of a strong acid such as H$_2$SO$_4$, HCl, HBr, HClO$_3$ or H$_3$PO$_4$ at a temperature from about 90° to 130° C. U.S. Pat. No. 3,753,991 further discloses the use of a strong base at a temperature of 130° to 190° C. during deacetylation in place of the strong acid.

In both patents the starting N-acetoacetylanthranilic acid ester is made through the reaction of the corresponding alkyl anthranilate with diketene.

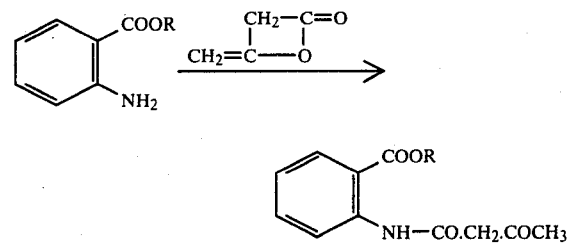

DESCRIPTION OF THE INVENTION

This invention relates to a process for the preparation of compounds which are dihydroxyquinoline and certain derivatives thereof. The compounds have the following formula:

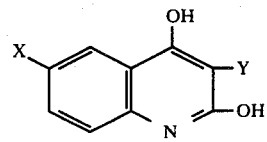

Where
X=Cl, BR, I, NO$_2$, H
Y=—CN, H, —COOH

The process of this invention is based on chemical reactions comprising the alkaline catalyzed condensation of isatoic anhydride or of certain ones of its derivatives with an alkyl ester of cyanoacetic acid to form 2-(2'-aminobenzoyl)cyanoacetate as illustrated by the following equation:

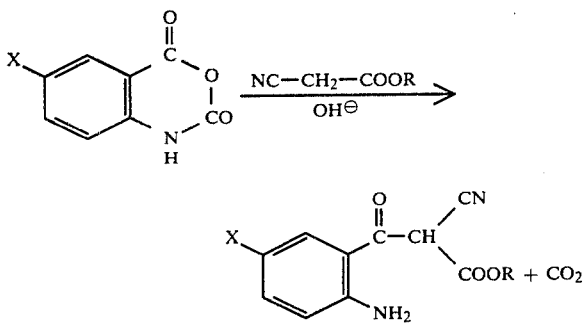

In the foregoing equation R is a straight or branched alkyl group containing 1 to 5 carbon atoms and X is as defined above.

The process reaction proceeds smoothly and nearly quantitatively at temperatures from room temperature to approximately 100° C. depending mainly on the chemical character of the substituent X and partly on the number of carbon in R of the cyanoacetate as further discussed hereinafter and illustrated in the examples.

The resulting 2-(2'-aminobenzoyl)cyanoacetate is an intermediate compound which subsequently undergoes cyclization, generally under conditions of heat and alkaline pH, to form 3-cyano-2,4-dihydroxyquinoline (when X is hydrogen) or its derivatives (where X is Cl, Br, I or $NO_2$). The following equation is illustrative:

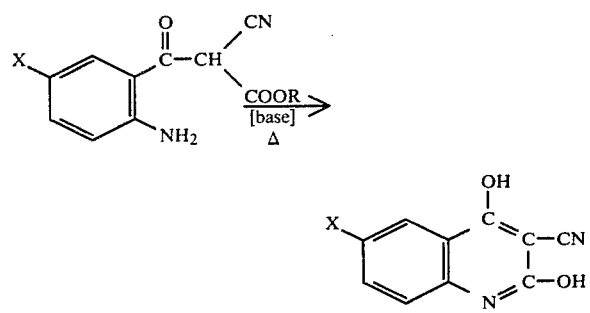

The ring closure depends strongly on the character of the substitution on the benzene ring. For example where X is hydrogen, chloride, bromine, or iodine, the intermediate 2-(2'-aminobenzoyl)cyanoacetate closes immediately with a minimum of heat. However, if X is $NO_2$ heating in the presence of a strong base is necessary.

Thus, the condensation of 5-nitroisatoic anhydride with methyl cyanoacetate under the catalytic action of triethylamine produces exclusively 2-(2'-amino-5'-nitrobenzoyl)cyanoacetate. The subsequent cyclization to 3-cyano-2,4-dihydroxy-6-nitroquinoline requires further treatment with sodium methoxide.

The 3-cyano-2,4-dihychoxyquinoline can be decyanated under either basic or acidic conditions. For example, if 2,4-dihydroxyquinoline or one of its 6-substituted derivatives is the desired final product, the cyano group can be cleaved under alkaline conditions at elevated temperatures to convert Y from —CN to —H. Cleavage can be accomplished in an aqueous solution of alkali metal hydroxide at a temperature from about 100° to 200° C. in an autoclave.

The decyanation also occurs under acid condition, to convert Y from —CN to —COOH, requiring heating with a strong acid such as sulfuric acid.

The alkaline decyanation offers a further advantage in that the formed 2,4-dihydroxyquinoline compound in the form of its disodium salt may be isolated and crystallized from its concentrated aqueous solutions, represented by the contents of the autoclave after the decyanation. This form is due to its good solubility in water, a preferred raw material in the production of azo dyes or pigments.

The condensation of isatoic anhydride or one of its derivatives with cyanoacetate can be carried out in a medium of any of several different solvents, or without the use of any solvent; the reaction can be catalyzed by any of a broad variety of bases, organic and inorganic. The degree of catalytic action of bases depends not only on their basic strength, but also on their solubility in the reaction medium. It is, therefor, not suprisingly that the bases which are soluble in the reaction medium have the strongest action. It is known* that primary and secondary aliphatic and aromatic amines react with isatoic anhydride, forming the corresponding anthranilamides and o-carboxyphenylureas; consequently they are not suitable bases. Similar complications, i.e., the formation of by-products, are connected with the use of primary or secondary alkali metal alcoholates.

* J.O.C. 18, pp. 1427–1439 Robert P. Staiger and Wagner. J.O.C. 9, pp. 55–67. Robert H. Clark.

The best results have been achieved using tertiary amines, e.g., trimethylamine, triethylamine, tripropylamine, triethanolamine, etc., pyridine and its alkyl derivatives, etc.

The most effective inorganic bases have been found to be the hydroxides and carbonates of alkali metals, while oxides and hydroxides of alkali earth metals are rapidly deactivated, due to fast formation of the corresponding carbonates ($CO_2$ from isatoic anhydride), insoluble in the reaction medium.

In one best mode and embodiment of this invention, triethylamine in an amount of one mole per mole of isatoic anhydride has been found to be an ideal base for the desired reaction. At the beginning of the condensation process it serves as a reaction medium, helping to fluidize the reacting mass. At the end of the condensation, the product, which is the triethylammonium salt of the quinoline derivative is a syrupy consistency, remaining easily stirrible and transferable into the equipment of the next step. In certain cases, especially when higher fluidity is required, an excess of triethylamine is used advantageously. This excess is then easily recoverable by a simple distillation. It has also been found that at least 85 percent of the required one mole of triethylamine per mole of isatoic anhydride can be recovered after alkalization of the final reaction mixture with aqueous NaOH or KOH, by phase separation combined with steam distillation. The reaction with other organic bases is slower, while inorganic bases usually require a medium of DMF (dimethylformamide), DMAC (dimethylacetamide), DMSO (dimethylsulfoxide), or NMP (N-methylpyrrolidone). Conducted in organic hydrocarbons and glycol ethers the reaction is extremely slow and the yields of desired product are usually lower.

It has been found that an addition of a small amount of DMF or DMAC, helps to accelerate the condensation in all investigated systems.

The theoretical amount of a cyanoacetate is preferably used in the process of the instant invention i.e. 1 mole per mole of isatoic anhydride condensate. If the alkyl cyanoacetate is used in a large excess in order to increase stirribility, there are substantial losses of the used cyanoacetate due to polymerization and chemical degradation. However a small excess of an alkyl cyanoacetate ester amounting to about a 2 to 5 mole percent excess over the theoretic amount favors slightly higher yields of the desired condensation product in shorter reaction time.

As already mentioned the decyanation of the quinoline ring can be carried out in an aqueous base such as sodium or potassium hydroxide at a temperature of about 100° to 200° C., preferentially from 130° to 160° C. The optimum amount of base for decyanation of any given quinoline compound varies depending primarily on the concentration, i.e. on the amount of water used; secondly on the temperature and time applied; and thirdly on the presence of other compounds which might cause undesired consumption of the base.

Regarding the first influential factor, it is preferred not to use more than 600 ml water per 1.0 gram mole of starting isatoic anhydride. In this case the required amount of base is about 2.5 to 3.5 moles and if the temperature applied is about 140° to 155° C., the process will take from 2.5 to 3 hours. Higher dilution requires more base or a substantially prolonged heating period. The same is true if a lower temperature than indicated is applied.

If an inorganic base is used as a condensation agent, the amount of base required for decyanation can be lowered by discounting the equivalents of base used for the condensation from the amount normally required by the decyanation process. It is also advisable to remove as much of the DMF or DMAC, if used, from the condensation product as feasible. Otherwise, the following reaction will consume the base necessary for decyanation.

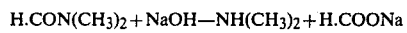

H.CON(CH$_3$)$_2$+NaOH—NH(CH$_3$)$_2$+H.COONa

If these solvents are not recovered, each mole of amide remaining during the decyanation process requires one additional mole of alkali hydroxide.

ThE EXAMPLES

The following examples represent the best presently known modes and embodiments in the practice of this invention.

EXAMPLE 1

Preparation of 2,4-Dihydroxyquinoline

Into a 150 ml three neck flask, equipped with an agitator, a reflux condenser sealed on its upper end with a gas bubbler, a thermometer and an electric heating mantle was charged 16.3 g pure isatoic anhydride (M.W. 163) 10.1 g triethylamine (M.W. 101), 9.9 g methyl cyanoacetate (M.W. 99) and 2 ml DMF. The reaction mixture, under agitation, was kept at a temperature within the range of 25° to 30° C. for approximately 1 hour. During this period a constant evolution of gas was observed. The temperature of the reaction mixture was then elevated to and maintained at 78° to 80° C. for approximately 2 hours. At the end of this heating period the evolution of gas practically stopped and the reaction mixture turned into a slightly yellow, good stirrable oil. A minimum of water (approximately 40 ml) and the still hot oil were transferred to a 300 ml stainless steel autoclave, equipped with an anchor agitator, a pressure gauge, a thermocouple and a vent-valve. A charge of 14.7 g sodium hydroxide (MW 40) pellets was added to the reaction mixture and the autoclave was closed. The contents of the autoclave, under agitation, were heated to and maintained at a temperature in the range of 150° to 155° C. for 3 hours. The pressure in the autoclave reached 275 to 280 psig during the heating; after cooling to 50° to 60° C. hot water was added to the autoclave and approximately 600 ml of a brownish colored solution was removed therefrom and treated with 1 g activated charcoal at 60° C. A slightly yellowish colored solution which resulted was then acidified with concentrated hydrochloric acid to a pH of approximately 2. White, slightly creamy colored precipitate which formed was recovered by filtration; the precipitate was then reslurried in 200 ml water, refiltered and dried at 110° C. The yield was 14.17 g (87.9 percent of theory based upon the isatoic anhydride charged) 2,4-dihydroxyquinoline, melting point 350°–355° C. Examination of the product by infrared spectroscopy and nuclear magnetic resonance indicated that it was of high purity.

EXAMPLE 2

Preparation of 3-Cyano-2,4-dihydroxyquinoline

A three neck flask, equipped as described in Example 1, was charged with 162.1 g pure isatoic anhydride, (molecular weight 163), 124.4 g ethyl cyanoacetate (molecular weight 113), 400 ml of triethylamine (molecular weight 101, specific gravity 20/20 0.729), and 12 drops of DMF. The charge was kept at a temperature in the range of 20°–25° C. with agitation, for 2 hours. A steady and rapid evolution of gas occurred throughout the reaction period. The reaction mixture went through a series of physical changes during this time, evidenced by changes of its fluidity and by gradual disappearance of an initial solid phase and appearance of another solid phase. The temperature was gradually raised to approximately 85° over a period of about 30 minutes, and maintained at this level for one additional hour. During this period the evolution of gas gradually slowed and finally stopped. At the end of this last heating period there was virtually no solid phase evident in the reaction mixture. After agitation was stopped, the reaction mixture separated into two layers, a colorless upper layer consisting mainly of triethylamine and a lower one, which was a golden viscous oil. The excess of triethylamine over one equivalent, which had been used as a diluent for the reaction mixture, was recovered by distillation, yield approximately 95 percent. Hot water was added to the remaining oil and the solution (2500 ml) which resulted was transferred to a 4 l beaker. Concentrated hydrochloric acid at a temperature of 60° to 70° C. was then added to the beaker to bring the pH to 1.0 and to form a precipitate. The precipitate was recovered by filtration; the filter cake was washed with water, was reslurried in 1500 ml of water at about 65° C., refiltered, rewashed and finally dried at 110° C. The yield was 181.3 g (97.4 percent of theory, based upon the isatoic anhydride charged) 3-cyano-2,4-dihydroxyquinoline, melting point 275°–277° C. Examination of the product by infrared spectroscopy and nuclear magnetic resonance indicated that it was of high purity.

EXAMPLE 3

Preparation of 6-chloro-3-cyano-2,4-dihydroxyquinoline

A 300 ml, three neck flask, equipped as described in Example 1, was charged with 39.5 g 5-chloroisatoic anhydride (molecular weight 198.5:assay 95 percent), 21.8 g methyl cyanoacetate, 150 ml triethylamine and four drops of DMF. Agitation was commenced, and continued until reaction was discontinued. A slight exotherm caused the temperature of the reaction mixture to increase from 20° C. to about 38° C., and to remain at about 38° C. for approximately one hour, during which time there was a steady and vigorous evolution of gas. At the end of one hour the temperature began to drop, and the rate of gas evolution slowed as the consistency of the reaction mixture became jelly-like. The reaction mixture was then heated to a temperature of 90° C. and maintained at a temperature within the range of 85° to 90° C. for one-half hour. The heating to 90° C. occurred over a period of one-half hour. The temperature of the reaction mixture was then raised to approximately 100° C., and maintained at about such temperature for an additional 30 minutes. Gas evolution reached a maximum during the time that the reaction mixture was at a temperature between 85° and 100° C. and then gradually decreased and stopped. The reaction mixture became jelly-like and gummy during the time that the temperature was being maintained between 85° and 90° C.; to facilitate stirring a 20 ml addition of DMF was made when this occurred. After the reaction mixture had been maintained at approximately 100° C. for one-half hour, agitation was stopped and the reaction mixture separated into an upper colorless layer consisting mainly of triethylamine and a lower layer of a tan oil. The excess of triethylamine was recovered by distillation, after which the oily remainder was dissolved in 700 ml water and treated with 3 g activated charcoal at reflux. Concentrated hydrochloric acid at a temperature of 60° to 70° C. was then added to the beaker to bring the pH to 1.0 and to form a precipitate. The precipitate was recovered by filtration; the filter cake was washed with water, was reslurried in warm water, refiltered, and finally dried at 60° C. The yield was 39.34 g (93.9 percent of theory based upon the pure 5-chloroisatoic anhydride charged) 6-chloro-3-cyano-2,4-dihydroxyquinoline, melting point 275°–277° C. Examination of the product by infrared spectroscopy and nuclear magnetic resonance indicated that it was of high purity.

EXAMPLE 4

Preparation of 2-(2'-amino-5'-nitrobenzoyl)cyanoacetate, methyl ester

A 300 ml, three neck flask, equipped as described in Example 1, was charged with 41.6 g 5-nitroisatoic anhydride (molecular weight 209:assay approximately 93 percent), 21.8 g methyl cyanoacetate, 150 ml triethylamine and four drops of DMF. The reaction was carried out in a period of 75 minutes, during which time the temperature was gradually increased from room temperature of about 20° C. to a maximum of 88° C. A steady and rapid evolution of gas occurred during about the first two-thirds of the reaction period; during the last one-third gas evolution decreased gradually and ultimately stopped altogether. Excess triethylamine was then stripped from the reaction mixture by distillation, maximum pot temperature 115° C. An oil, golden-brown in color, which remained was dissolved in approximately 200 ml hot water. An insoluble brown polymeric material which formed was removed by filtration through diatomaceous earth. The solution was then treated with activated carbon, and acidified to a pH of 1.0 with concentrated hydrochloric acid to precipitate methyl 2-(2'-amino-5'-nitrobenzoyl)cyanoacetate. The product was worked-up and recovered as described above in the previous Examples. The yield was 39.34 g (93.9 percent of theory based upon the pure 5-nitroisatoic anhydride charged), melting point 275°–277° C. Examination of the product with infrared spectroscopy and nuclear magnetic resonance indicated that it was of high purity.

EXAMPLE 5

Preparation of 3-Cyano-2,4-dihydroxy-6-nitroquinoline

A 13.16 g portion of the methyl 2-(2'-amino-5'-nitrobenzoyl)cyanoacetate, produced as described in Example 4 (molecular weight 263) was cyclized by refluxing for 8 hours with 2.81 g sodium methoxide (molecular weight 54) in 60 ml pyridine. After cyclization the pyridine was distilled and the batch was worked up as described above in Example 3. That part of the reaction product which was water insoluble before the acidification was not the desired quinoline derivative and was discarded. The precipitate which formed after acidification of the clear yellowish-brown mother liquor to pH 2.5 was found by infrared spectroscopy and nuclear magnetic resonance to be the crude desired product (melting point 281°–282° C.). The yield was 7.5 g, 64.9 percent of theory based on starting methyl ester of 2-(2'-amino-5'-nitrobenzoyl) cyanoacetate.

EXAMPLE 6

Preparation of 2,4-Dihydroxyquinoline

A 200 ml three neck flask, equipped as described previously was charged with 16.3 g isatoic anhydride, 9.9 g methyl cyanoacetate, 8.3 g anhydrous potassium carbonate (molecular weight 138.2), and 16 g DMF. The reaction mixture was agitated at 28° to 30° C. for 1 hr. There was a slow evolution of gas during this period. The temperature was then gradually raised to 90° C. over a period of 90 minutes and kept at 90° C. for an additional 15 minutes. The gas evolution, which became strong and steady at the elevated temperature, gradually came to a stop at the end of the heating period. The reaction mixture, while still hot, was then dissolved in a charge of 60 ml of water and transferred into a 300 ml autoclave; an additional 20 ml portion of water was used to wash the flask. A 12 g charge of sodium hydroxide (molecular weight 40) pellets was added: the autoclave was closed, and heated at 135° to 140° C. with constant agitation for four hours. The desired product was isolated as described in Example 1. The yield was 12.93 g pure 2,4-dihydroxyquinoline (m.p. 353°–355° C.), 80.23 percent of theory based on isatoic anhydride.

EXAMPLE 7

Preparation of Sodium Salt of Dihydroxyquinoline

Following in principle the procedure described in Example 1, 32.6 g isatoic anhydride was condensed with 20.8 g methyl cyanoacetate in the presence of 20.20 g of triethylamine and 2 ml of DMF.

At the end of the decyanation process, the contents of the autoclave were cooled to 60° to 70° C., the autoclave was opened, and the slurry of the product was recovered by filtration. The filter cake was washed with 20 ml ice cold water and dried at 100° C. to a constant weight. The yield was 31.0 g crude sodium salt of 2,4-dihydroxyquinoline.

The autoclave was then washed; the washings were combined with mother liquor from the previous filtration and with washings from the filter cake. The combined washings were acidified with concentrated hydrochloric acid to form a precipitate, which was then recovered by filtration, washed, and dried at 100° C. The yield was 3.92 g pure 2,4-dihydroxyquinoline (m.p. 355° C.), 12.25 percent of theory based on the isatoic anhydride charged.

To determine the overall balance of the process, a 5 g portion of the previously recovered sodium salt was dissolved in water and 2,4-dihydroxyquinoline was precipitated, yield 4.0 g pure 2,4-dihydroxyquinoline. Accordingly, the 31.0 g recovery of sodium salt represented 24.8 g 2,4-dihydroxyquinoline, 76.94 percent of theory, so that the total yield of 2,4-dihydroxyquinoline was = 89.19 percent

I claim:

1. A process for preparing 3-cyano-2,4-dihydroxyquinolines having the formula

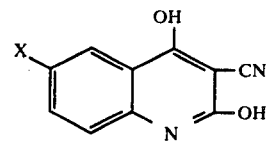

where X is Cl, Br, I, $NO_2$, or H, which process comprises the steps of (a) reacting isatoic anhydride or the corresponding chloro, bromo, iodo or nitro derivative thereof with a C-1 to C-5 alkyl ester of cyanoacetic acid in the presence of a base which is not reactive with the anhydride to form a 2-(2'-aminobenzoyl) cyanoacetate as an intermediate compound, and (b) cyclizing the intermediate cyanoacetate to form the 3-cyano-2,4-dihydroxyquinoline.

2. A process as claimed in claim 1 which includes the additional step of hydrolyzing the cyano group of the 3-cyano-2,4-dihydroxyquinoline under acid conditions to convert the —CN to —COOH.

3. A process as claimed in claim 1 which includes the additional step of hydrolyzing the cyano group of the 3-cyano-2,4-dihydroxyquinoline under alkaline conditions to convert the —CN to —H.

* * * * *